(12) United States Patent
Dou et al.

(10) Patent No.: US 11,149,048 B2
(45) Date of Patent: Oct. 19, 2021

(54) HIGH-PURITY D-PSICOSE PREPARATION METHOD

(71) Applicant: SHANDONG BAILONG CHUANGYUAN BIO-TECH CO., LTD, Yucheng (CN)

(72) Inventors: Baode Dou, Yucheng (CN); Guangpeng Dou, Yucheng (CN); Mingzhan Zhang, Yucheng (CN); Xianbao Shao, Yucheng (CN); Fanghua Li, Yucheng (CN); Qian Du, Yucheng (CN); Tengteng Yang, Yucheng (CN)

(73) Assignee: SHANDONG BAILONG CHUANGYUAN BIO-TECH CO., LTD, Yucheng (CN)

( * ) Notice: Subject to any disclaimer, the term of this patent is extended or adjusted under 35 U.S.C. 154(b) by 132 days.

(21) Appl. No.: 16/466,060

(22) PCT Filed: Dec. 1, 2017

(86) PCT No.: PCT/CN2017/114289
§ 371 (c)(1),
(2) Date: Jun. 3, 2019

(87) PCT Pub. No.: WO2018/099479
PCT Pub. Date: Jun. 7, 2018

(65) Prior Publication Data
US 2020/0062792 A1  Feb. 27, 2020

(30) Foreign Application Priority Data
Dec. 2, 2016  (CN) .......................... 201611095914.6

(51) Int. Cl.
*C07H 1/08* (2006.01)
*C07H 3/02* (2006.01)
*C12P 19/02* (2006.01)
*C12P 19/24* (2006.01)

(52) U.S. Cl.
CPC .............. *C07H 1/08* (2013.01); *C07H 3/02* (2013.01); *C12P 19/02* (2013.01); *C12P 19/24* (2013.01); *C07B 2200/13* (2013.01)

(58) Field of Classification Search
CPC ... C07H 1/08; C07H 3/02; C12P 19/24; C12P 19/02; C07B 2200/13

USPC ........................................................ 536/127
See application file for complete search history.

(56) References Cited

U.S. PATENT DOCUMENTS

| 8,735,106 B2 | 5/2014 | Hong et al. |
| 9,988,618 B2 | 6/2018 | Kim et al. |
| 2011/0237790 A1* | 9/2011 | Lee .......................... C07H 1/06 536/127 |

FOREIGN PATENT DOCUMENTS

| CN | 102869783 A | 1/2013 |
| CN | 103333935 A | 10/2013 |
| CN | 105602879 A | 5/2016 |
| CN | 105802897 A | 7/2016 |
| CN | 106164265 A | 11/2016 |
| CN | 106520746 A | 3/2017 |

OTHER PUBLICATIONS

Zhang et al. Recent advances in D-allulose: Physiological functionalities, applications, and biological production. Trends in Food Science & Technology 54 (2016) 127-137. Available online Jun. 9, 2016 (Year: 2016).*
International Search Report from International Application No. PCT/CN2017/114289, dated Feb. 26, 2018.
Written Opinion from International Application No. PCT/CN2017/114289, dated Feb. 26, 2018.

* cited by examiner

*Primary Examiner* — Yih-Horng Shiao
(74) *Attorney, Agent, or Firm* — Merchant & Gould P.C.

(57) ABSTRACT

A method for preparing high-purity D-psicose, comprising the following steps: (1) centrifuging a fermentation broth of *Bacillus subtilis*, and then subjecting the bacteria to homogenization to obtain a mixed solution containing D-psicose 3-epimerase; (2) preparing a fructose solution, adding the mixed solution containing D-psicose 3-epimerase to the fructose solution, adjusting the pH, adding cobalt chloride thereto, and performing the reaction at a certain temperature; and feeding the fructose solution to the reaction solution, continuing the reaction, and stopping the reaction, obtaining a crude D-psicose solution; and (3) subjecting the crude D-psicose solution to decolorization, filtration, ion exchange, chromatographic separation, concentration, and then crystallization or drying, obtaining D-psicose.

10 Claims, No Drawings

HIGH-PURITY D-PSICOSE PREPARATION METHOD

This application is a National Stage Application of PCT/CN2017/114289, filed 1 Dec. 2017, which claims benefit of Serial No. 201611095914.6, filed 2 Dec. 2016 in China and which applications are incorporated herein by reference. To the extent appropriate, a claim of priority is made to each of the above disclosed applications.

TECHNICAL FILED

The present application relates to a method for preparing a high-purity D-psicose, and belongs to the field of biotechnology.

BACKGROUND ART

D-psicose is an important, rare sugar which is present in nature in a trace amount in cane molasses, dried fruits, sugar products, wheat and *Itea* plants. Its name originated from the fact that a small amount of D-psicose can be isolated from antibiotic psicofuranine. D-psicose is absorbed in the small intestine to enter into the blood circulation in the human body, and will not be metabolized into energy after absorption in the small intestine, and has a low fermentative availability for intestinal microorganisms. D-psicose has a variety of important physiological functions: neuroprotection, reducing blood sugar levels, lowering fats, scavenging reactive oxygen species, anti-oxidation, inhibiting cancer cell proliferation, acting as a low-calorie sweetener, and the like.

D-psicose exerts the function of neuroprotection by increasing the level of intracellular glutathione, has the function of reducing blood sugar levels, lowering fats, and improving quality of product as well as anti-oxidation. As a sweetener, D-psicose has a sweetness equivalent to 70% of that of fructose and an energy of only 0.3% of that of sucrose. D-psicose produces little energy and is not toxic to growth of mice. Compared with fructose, D-psicose can inhibit the activity of lipese in liver of mice and reduce the accumulation of abdominal fats, and can be used as a sweetener in assisting weight reduction. D-psicose shows a strong ability to scavenge reactive oxygen species, having a potential medical value in the prevention and treatment of various diseases.

The Chinese patent document CN105602879A (which has an application number of 201610051547.3) disclosed a genetically engineered strain that is capable efficiently secreting D-psicose 3-epimerase and a method of constructing the same. In the invention, a recombinant expression plasmid pMA5-RDPE was reconstructed by using the D-psicose 3-epimerase gene rdpe from *Ruminococcus* sp. 5_1_39B_FAA, and *Bacillus subtilis* was transformed with the recombinant expression plasmid, thereby achieving the constitutive secretion and expression of RDPE in the *Bacillus subtilis*. By comparing three sugar-inducible promoters, PxylA was identified as the optimal inducible promoter and the secretion level of RDPE was significantly increased. By knocking out the xylose utilization gene xylAB (xylA and xylB), the xylose metabolism pathway of *Bacillus subtilis* was blocked, and the secretion level of RDPE was further increased, and the optimal induction concentration of the inducer xylose was reduced from 4.0% to 0.5%. Finally, the engineered strain 1A751SD-XR was evaluated in a 7.5 L fermentation tank by means of fed-batch fermentation, and the secretion level of RDPE was up to 95 U/mL and 2.6 g/L. However, the enzyme activity of the enzyme was still low and could not meet the needs of actual production.

At present, there are problems such as low conversion rate and easy decomposition for D-psicose, and thus the application fields of D-psicose are greatly limited, and characteristics of the product itself are difficult to be shown effectively.

CONTENTS OF THE INVENTION

The present invention provides a method for preparing a high-purity D-psicose to address the deficiencies in the prior art.

The technical solution of the present invention is as follows:

A method for preparing D-psicose comprising the following steps:

(1) centrifuging a fermentation broth of *Bacillus subtilis*, and then subjecting the bacteria to homogenization to obtain a mixed solution containing D-psicose 3-epimerase;

said *Bacillus subtilis* being a *Bacillus subtilis* strain BLCY-005, which was deposited in the China General Microbiological Culture Collection Center, Institute of Microbiology, Chinese Academy of Sciences (Address: No. 1-3, Beichen West Road, Chaoyang District, Beijing) on Oct. 26, 2016, and has an accession number of CGMCC No. 13152.

(2) preparing a fructose solution having a mass concentration of 20% to 60%, adding the mixed solution containing D-psicose 3-epimerase to the fructose solution, adjusting the pH to 5.5-6.5, adding 0.001%-0.005% by mass of cobalt chloride thereto, and performing the reaction at 40-60° C. for 10 to 30 hours; and feeding the fructose solution to the reaction solution to maintain the concentration of fructose in the reaction system at 20% to 60%, continuing the reaction for 10 to 30 hours, and stopping the reaction, obtaining a crude D-psicose solution; and (3) subjecting the crude D-psicose solution prepared in step (2) to decolorization, filtration, ion exchange, chromatographic separation, concentration, and then crystallization or drying to obtain D-psicose.

According to a preferred embodiment of the present invention, in step (1), the centrifugation is carried out at a temperature of 10 to 20° C. and a rotation speed of 3000 r/min for a period of 30 to 50 minutes.

According to a preferred embodiment of the present invention, in step (1), the homogenization is carried out at a temperature of 10 to 20° C. and a pressure of 30 MPa to 50 MPa for a period of 10 to 20 minutes.

According to a preferred embodiment of the present invention, in step (1), the fermentation broth of *Bacillus subtilis* is prepared by a method below:

I. the *Bacillus subtilis* BLCY-005 is inoculated in a seed culture medium, and cultivated at 30 to 38° C. for 6 to 12 hours to prepare a seed liquid;

wherein said seed culture medium comprises the following components in a weight percentage: 1% of peptone, 0.5% of a yeast extract powder, 1% of sodium chloride, 0.01% of anhydrous magnesium sulfate, 0.02% of potassium dihydrogen phosphate, and the balance of water, with a pH of 6.0-7.0;

II. the seed liquid prepared in step I is inoculated in a fermentation culture medium in an amount of 1 to 10% by volume, and fermented at 30 to 38° C. for 30 to 48 hours to prepare the fermentation broth of *Bacillus subtilis*; wherein said fermentation culture medium comprises the following components in a weight percentage: 3% of a yeast extract powder, 2% of corn syrup powder, 1% of glucose, 0.01% of anhydrous magnesium sulfate, 0.02% of diammonium phosphate, 0.02% of ammonium sulfate, and the balance of water, with a pH of 6.0-7.0.

According to a preferred embodiment of the present invention, in step (2), the mixed solution containing D-psicose 3-epimerase is added in an amount of 5% by volume based on the fructose solution.

According to the preferred embodiment of the present invention, in step (3), the decolorization step is as follows:

0.5 to 1% by mass of activated carbon is added to the crude D-psicose solution prepared in step (2), and stirred at 80 to 85° C. for 30 to 40 minutes.

According to the preferred embodiment of the present invention, in step (3), the filtration is carried out by means of plate and frame filtration at pressure of 0.2-0.4 MPa and a water flow rate of 5.0-6.0 t/h.

According to the preferred embodiment of the present invention, in step (3), the ion exchange step is as follows:

the decolorized and filtered crude sugar liquid is subjected to desalination by ion exchange in a continuous ion exchange system at a flow rate of a volume as 3 times as resin volume per hour at 35 to 55° C. The transmittance of the liquid after the ion exchange is ≥98%. The treated liquid is clear and transparent, and has no odor.

According to the preferred embodiment of the present invention, in step (3), the chromatographic separation is as follows:

the chromatographic separation is carried out at a pressure of 0.20 to 0.30 MPa, a temperature of 60 to 70° C., a water consumption ratio of 1:(1.3~1.6), and a feeding rate of 1.5 to 2.0 m³ per hour, and D-psicose is collected.

According to the preferred embodiment of the present invention, in step (3), the concentration is carried out in a four-effect falling film evaporator at a vacuum of 0.06-0.09 MPa and a feeding temperature of 50-85° C., and the liquid is concentrated to 60-75% of the original volume.

According to the preferred embodiment of the present invention, in step (3), the drying is a spray drying as follows:

the concentrated sugar liquid is fed to a drying tower, wherein the inlet air temperature is 130-150° C., the atomizer is initialized, and the liquid is spray-dried into a powdery solid.

According to the preferred embodiment of the present invention, in step (3), the crystallization reaction conditions are as follows: the mass concentration of the sugar liquid is 70 to 85%, and the temperature is 50 to 70° C.; and a seed crystal of 10 to 30% by mass of the solute is added, stirred uniformly, allowed to stand at 50 to 70° C. for 8 to 16 hours, then slowly cooled down at a rate of 1° C./3~6 h while slowly stirring until a large amount of uniform and regular crystal grains are formed in the solution, and separation is carried out to obtain D-psicose.

ADVANTAGEOUS EFFECTS

1. In the present invention, a *Bacillus subtilis* stain is isolated from the soil, and is subjected to mutagenesis treatments such as ultraviolet mutagenesis and nitrosoguanidine mutagenesis. Finally a high-potency strain (named as BLCY-005) that is capable of producing D-psicose epimerase in a high yield was obtained, which strain has an enzyme activity of up to 143 U/ml which is higher than the activity of a traditional D-psicose epimerase by 50%, greatly improving the ability to covert sucrose to D-psicose. At the same time, a process for feeding fructose is employed, whereby the D-psicose content in the final product is up to 99%, which is significantly higher than that in a product obtained in the prior art, significantly lowering the production cost. Compared with a D-psicose epimerase production by a traditional strain which has an optimum pH of neutrality, the optimum pH value of the present production method is 5.5-6.5, thereby facilitating the control of pollution in production.

2. In the present invention, a fermentation broth of *Bacillus subtilis* is directly used for the preparation, and the process of extracting the enzyme is omitted, greatly lowering the production cost, wherein the cost is reduced by about 25% compared with the traditional production method, and markedly enhancing the competitiveness of product.

3. In the present invention, by using a D-psicose epimerase which is significantly higher in activity than the existing enzymes and by adjusting the process steps and parameters, a high-purity D-psicose is prepared; as a low-calorie sweetener, the D-psicose can be widely used in the fields including foods, beverages, cosmetics, medicines and like. The large-scale industrial production of D-psicose is achieved, significantly lowering the production cost of D-psicose, and expanding application scope of D-psicose.

SPECIFIC MODE FOR CARRYING OUT THE INVENTION

The technical solutions of the present invention are further described below in conjunction with the examples, but the protection scope of the present invention is not limited thereto.

Example 1

The *Bacillus subtilis* strain BLCY-005 was deposited in the China General Microbiological Culture Collection Center, Institute of Microbiology, Chinese Academy of Sciences (Address: No. 1-3, Beichen West Road, Chaoyang District, Beijing) on Oct. 26, 2016, and has an accession number of CGMCC No. 13152.

The original strain of the *Bacillus subtilis* strain BLCY-005 according to the present invention was isolated from the soil near the pilot plant of Bailong Chuangyuan in Dezhou, Shandong Province, and obtained after mutagenesis. The specific isolating process was as follows.

Enrichment Culture

The surfacesoil of the soil near the research and development pilot plant of Bailong Chuangyuan in Dezhou, Shandong Province, was removed with a small shovel, about 10 g of the soil from 5-15 cm depth of the ground were diluted with sterile water by 10 folds, then a LB medium was added thereto for enrichment culture, and the incubation was carried out at 30 to 38° C. for 24 h.

Axenic Isolation

Using a streaking method, 2 ml of the bacterial solution after enrichment culture in step (1) were added to a large test tube containing 5 ml of sterile water to be diluted, and fully shaken and dispersed; a loop of the diluted liquid was picked up by a sterile operation using an inoculating loop; 3-4 parallel lines were firstly drawn on one side of a culture plate, the culture dish was rotated at an angle of about 60° C., and the residue on the inoculating loop was burn off. After cooling, the second streaking was performed by a method same as the first streaking method, and the third streaking and fourth streaking were performed in the same manner. After the streaking was completed, the culture dish was covered and inverted. After incubation at 28-38° C. for 24 h, a single colony was picked, inoculated in 10 slant cultures, and numbered as 01-10. The No. 01-10 slant seeds were inoculated in a culture medium in shake flasks and cultivated at 28-38° C. for 24 h. The conversion rate of D-fructose to D-psicose in a fermentation broth of each of the No. 01-10 shake flasks was measured, wherein the conversion rate in the No. 06 shake flask was the highest, up to 26.12%.

The composition of the culture medium in the culture plate was: 1% of peptone, 0.5% of a yeast extract powder and 1% of sodium chloride 1%, with a natural pH.

The composition of the culture medium in the shake flask was: 3% of a yeast extract powder, 2% of corn syrup powder, 1% of glucose, 0.01% of anhydrous magnesium sulfate, 0.02% of diammonium phosphate, 0.02% of ammonium sulfate, and the balance of water, with a pH of 6.0-7.0.

Mutagenesis Screening

The No. 06 strain was subjected to UV-induced mutagenesis, wherein the UV-induced mutagenesis was carried out by irradiating with 15 W ultraviolet at a distance of 20 cm for 120 s. The obtained high-potency strain was further subjected to nitrosoguanidine mutagenesis treatment. Finally a strain capable of producing D-psicose epimerase having a high conversion rate was obtained and named as BLCY-005. The D-psicose 3-epimerase produced by the strain BLCY-005 had an enzyme activity of up to 143 U/ml which is higher than 75 U/ml of a D-psicose 3-epimerase produced by a wild-type strain.

Method for determining the enzyme activity: 800 μl of a phosphate buffer, 50 ml of a solution of D-fructose in a concentration of 100 g/L and a pH of 7.0, and 200 μl of the fermentation broth were added to 1 ml of a reaction system, the temperature was kept at 55° C. for 10 minutes, and then boiled for 10 minutes to terminate the enzymatic reaction.

The yield of D-psicose was measured by HPLC to calculate the enzyme activity. The active unit (U) referred to an amount of the enzyme required to catalyze the production of 1 μmol of D-psicose per minute.

Ecological Form

The colony was dirty-white and translucent. The edge of the colony was irregular and wavy, and center thereof was highly convex. Observed by microscopy, the strain was about 1.0-1.5 microns long and about 0.6-0.9 microns wide and had no capsule and flagella, and the spores were located in the center of the strain or slightly off-centered. After the spores were formed, they were not inflated.

Example 2

A method for cultivating the Bacillus subtilis BLCY-005 as described in Example 1, comprised the following steps of:

(a) the Bacillus subtilis BLCY-005 was inoculated in a LB medium, and cultivated at 35° C. for 12 hours to prepare an activated strain;

(b) the activated strain obtained in step (a) was inoculated in a seed culture medium, and subjected to enrichment culture for 12 hours at 35° C. to obtain a seed liquid;

wherein said seed culture medium comprised the following components in a weight percentage: 1% of peptone, 0.5% of a yeast extract powder, 1% of sodium chloride, 0.01% of anhydrous magnesium sulfate, 0.02% of potassium dihydrogen phosphate, and the balance of water, with a pH of 6.8.

(c) the seed liquid prepared in step (b) was inoculated in a fermentation culture medium in an amount of 5% by volume, and subjected to expanding culture at 35° C. for 48 hours to obtain a fermentation broth of Bacillus subtilis;

wherein said fermentation culture medium comprised the following components in a weight percentage: 3% of a yeast extract powder, 2% of corn syrup powder, 1% of glucose, 0.01% of anhydrous magnesium sulfate, 0.02% of diammonium phosphate, 0.02% of ammonium sulfate, and the balance of water, with a pH of 6.8.

Example 3

A method for preparing D-psicose, the steps of which were as follows:

(1) The fermentation broth of Bacillus subtilis prepared in Example 2 was centrifuged at 20° C. and a rotation speed of 3000 r/min for 30 minutes, then the strains were homogenized at a temperature of 20° C. and a pressure of 30 MPa for 10 minutes to obtain a mixed solution containing D-psicose 3-epimerase;

(2) a fructose solution having a mass concentration of 60% was prepared, and to which the mixed solution containing D-psicose 3-epimerase was added in an amount of 5% by volume based on the fructose solution; the pH was adjusted to 5.5, 0.005% by mass of cobalt chloride was added, and the reaction was carried out at a temperature 40° C. for 30 hours; and the fructose solution was fed to the reaction solution maintaining the concentration of fructose in the reaction system at 20%, the reaction was continued for 30 hours, and the reaction was stopped to prepare a crude D-psicose solution; and (3) the crude D-psicose solution prepared in step (2) was subjected to decolorization, plate and frame filtration, ion exchange, chromatographic separation, concentration, and then crystallization or drying, obtaining D-psicose.

The decolorization step was as follows:

0.5% by mass of activated carbon was added to the crude D-psicose solution prepared in step (2), and stirred at 85° C. for 30 minutes.

The plate and frame filtration was carried out at pressure 0.4 MPa and a water flow rate of 5.0 t/h.

The ion exchange step was as follows:

the decolorized and filtered crude sugar liquid was subjected to desalination by ion exchange in a continuous ion exchange system at a flow rate of a volume as 3 times as resin volume per hour at 55° C., and the transmittance of the liquid after the ion exchange was of ≥98%.

The chromatographic separation step was as follows:

the chromatographic separation was carried out at a pressure of 0.20 MPa, a temperature of 70° C., a water consumption ratio of 1:1.3, and a feeding rate of 2.0 m$^3$ per hour, and D-psicose was collected.

The concentration is carried out in a four-effect falling film evaporator at a vacuum of 0.06 MPa and a feeding temperature of 85° C., and the liquid was concentrated to 60% of the original volume.

The drying was a spray drying as follows:

the concentrated sugar liquid was fed to a drying tower, wherein the inlet air temperature was of 150° C., the atomizer was initialized, and the liquid was spray-dried, thereby obtaining D-psicose.

After testing, the conversion rate was determined to be 42.58%, which was much higher than 26.12% in the original strain.

Example 4

A method for preparing D-psicose, the steps of which were as follows:

(1) The fermentation broth of *Bacillus subtilis* prepared in Example 2 was centrifuged at 10° C. and a rotation speed of 3000 r/min for 50 minutes, then the strains were homogenized at a temperature of 10° C. and a pressure of 50 MPa for 20 min to obtain a mixed solution containing D-psicose 3-epimerase;

(2) a fructose solution having a mass concentration of 20% was prepared, and to which the mixed solution containing D-psicose 3-epimerase was added in an amount of 5% by volume based on the fructose solution; the pH was adjusted to 6.5, 0.001% by mass of cobalt chloride was added, and the reaction was carried out at a temperature 60° C. for 10 hours; and the fructose solution was fed to the reaction solution to maintain the concentration of fructose in the reaction system at 60%, the reaction was continued for 10 hours, and the reaction was stopped to prepare a crude D-psicose solution; and (3) the crude D-psicose solution prepared in step (2) was subjected to decolorization, plate and frame filtration, ion exchange, chromatographic separation, concentration, and then crystallization or drying, obtaining D-psicose.

The decolorization step was as follows:

1% by mass of activated carbon was added to the crude D-psicose solution prepared in step (2), and stirred at 80° C. for 40 minutes.

The plate and frame filtration was carried out at pressure 0.2 MPa and a water flow rate of 6.0 t/h.

The ion exchange step was as follows:

the decolorized and filtered crude sugar liquid was subjected to desalination by ion exchange in a continuous ion exchange system at a flow rate of a volume as 3 times as resin volume per hour at 35° C., and the transmittance of the liquid after the ion exchange was ≥98%.

The chromatographic separation step was as follows:

the chromatographic separation was carried out at a pressure of 0.30 MPa, a temperature of 60° C., a water consumption ratio of 1:1.6, and a feeding rate of 1.5 m³ per hour, and D-psicose was collected.

The concentration is carried out in a four-effect falling film evaporator at a vacuum of 0.09 MPa and a feeding temperature of 50° C., and the liquid was concentrated to 75% of the original volume.

the crystallization was carried out under the following reaction conditions: the mass concentration of the sugar liquid was of 70%, and the temperature was of 70° C.; and, a seed crystal of 10% by mass of the solute was added, stirred uniformly, allowed to stand at 70° C. for 8 hours, then slowly cooled down at a rate of 1° C./6 h while slowly stirring until a large amount of uniform and regular crystal grains were formed in the solution, and separation was carried out, obtaining D-psicose.

After testing, the conversion rate was determined to be 43.12%, which was much higher than 26.12% in the original strain.

What is claimed is:

1. A method for preparing D-psicose, comprising the following steps:
   (1) centrifuging a fermentation broth of *Bacillus subtilis*, and then subjecting the *Bacillus subtilis* bacteria to homogenization to obtain a mixed solution containing an enzyme to produce D-psicose;
   said *Bacillus subtilis* being a *Bacillus subtilis* strain BLCY-005:
   (2) preparing a fructose solution having a mass concentration of 20% to 60%, adding the mixed solution containing the enzyme to produce D-psicose to the fructose solution, adjusting the pH to 5.5-6.5, adding 0.001%-0.005% by mass of cobalt chloride thereto, and performing the reaction of the enzyme to produce D-psicose from fructose at 40-60° C. for 10 to 30 hours; and feeding additional fructose solution to the reaction to maintain the mass concentration of fructose in the reaction at 20% to 60%, continuing the reaction for 10 to 30 hours, followed by stopping the reaction, and obtaining a crude D-psicose solution; and
   (3) subjecting the crude D-psicose solution prepared in step (2) to decolorization, filtration, ion exchange, chromatographic separation, concentration, and then crystallization or drying to obtain D-psicose.

2. The preparing method according to claim 1, wherein in step (1), the centrifugation is carried out at a temperature of 10 to 20° C. and a rotation speed of 3000 r/min for a period of 30 to 50 minutes.

3. The preparing method according to claim 1, wherein in step (1), the homogenization is carried out at a temperature of 10 to 20° C. and a pressure of 30 MPa to 50 MPa for a period of 10 to 20 minutes.

4. The preparing method according to claim 1, wherein in step (1), the fermentation broth of *Bacillus subtilis* is prepared by a method below:
   (I) the *Bacillus subtilis* BLCY-005 is inoculated in a seed culture medium, and cultivated at 30 to 38° C. for 6 to 12 hours to prepare a seed liquid;
   wherein said seed culture medium comprises the following components in a weight percentage: 1% of peptone, 0.5% of a yeast extract powder, 1% of sodium chloride, 0.01% of anhydrous magnesium sulfate, 0.02% of potassium dihydrogen phosphate, and the balance of water, with a pH of 6.0-7.0;
   (II) the seed liquid prepared in step (I) is inoculated in a fermentation culture medium in an amount of 1 to 10% by volume, and fermented at 30 to 38° C. for 30 to 48 hours to prepare the fermentation broth of *Bacillus subtilis;*
   wherein said fermentation culture medium comprises the following components in a weight percentage: 3% of a yeast extract powder, 2% of corn syrup powder, 1% of glucose, 0.01% of anhydrous magnesium sulfate, 0.02% of diammonium phosphate, 0.02% of ammonium sulfate, and the remaining weight percentage of water, with a pH of 6.0-7.0.

5. The preparing method according to claim 1, wherein in step (2), the mixed solution containing the enzyme to produce D-psicose is added in an amount of 5% by volume based on the fructose solution.

6. The preparing method according to claim 1, wherein in step (3), the decolorization step is as follows: 0.5 to 1% by mass of activated carbon is added to the crude D-psicose solution prepared in step (2), and stirred at 80 to 85° C. for 30 to 40 minutes; and in step (3), the filtration is carried out by means of plate and frame filtration at pressure of 0.2-0.4 MPa and a water flow rate of 5.0-6.0 t/h to obtain a crude D-psicose liquid.

7. The preparing method according to claim 6, wherein in step (3), the ion exchange step is as follows: the decolorized and filtered crude D-psicose liquid is subjected to desalination by ion exchange in a continuous ion exchange system at a flow rate of 3× resin volume per hour at 35 to 55° C., and transmittance of the liquid after the ion exchange is ≥98%; and, in step (3), the chromatographic separation is as follows: the chromatographic separation is carried out at a pressure of 0.20 to 0.30 MPa, a temperature of 60 to 70° C., and a feeding rate of 1.5 to 2.0 m³ per hour, and a separated liquid containing D-psicose is collected.

8. The preparing method according to claim 1, wherein in step (3), the concentration is carried out in a four-effect falling film evaporator at a vacuum of 0.06-0.09 MPa and a feeding temperature of 50-85° C., to obtain a concentrated D-psicose liquid at 60-75% of the original volume.

9. The preparing method according to claim 8, wherein in step (3), the drying is a spray drying as follows: concentrated D-psicose liquid is fed to a drying tower, the inlet air temperature is of 130-150° C., the atomizer is initialized, and the liquid is spray-dried into a powdery solid.

10. The preparing method according to claim 8, wherein in step (3), the crystallization reaction conditions are as follows: the mass concentration of the concentrated D-psicose liquid is 70 to 85%, and the temperature is 50 to 70° C.; and, a seed crystal of 10 to 30% by mass of a D-psicose solute is added to form a crystallization solution, stirred uniformly, allowed to stand at 50 to 70° C. for 8 to 16 hours, then slowly cooled down at a rate of 1° C./3~6 h while slowly stirring until uniform crystal grains are formed in the crystallization solution, and separation is carried out to obtain a solid D-psicose.

* * * * *